United States Patent [19]

Thomas et al.

[11] Patent Number: 5,227,536
[45] Date of Patent: Jul. 13, 1993

[54] PROCESS FOR PREPARING HYDROXYBENZOCYCLOBUTENES

[75] Inventors: Pulikkottil J. Thomas; Robert A. DeVries; R. Garth Pews; Daniel A. Batzel, all of Midland, Mich.

[73] Assignee: The Dow Chemical Company, Midland, Mich.

[21] Appl. No.: 922,651

[22] Filed: Jul. 30, 1992

Related U.S. Application Data

[63] Continuation of Ser. No. 763,014, Sep. 20, 1991, abandoned.

[51] Int. Cl.$^5$ .................. C07C 39/17; C07C 37/02
[52] U.S. Cl. .................. 568/734; 568/731; 568/732; 568/796
[58] Field of Search .............. 568/716, 731, 732, 734, 568/796, 797; 560/8

[56] References Cited

U.S. PATENT DOCUMENTS

| | | | |
|---|---|---|---|
| 1,882,824 | 10/1932 | Hale | 568/797 |
| 2,028,065 | 1/1930 | Hale | 568/797 |
| 2,137,587 | 11/1938 | Poffenberger | 568/749 |
| 2,138,609 | 11/1938 | Meyer | 568/797 |
| 4,001,340 | 1/1977 | Smith et al. | 568/797 |
| 4,540,763 | 9/1985 | Kirchhoff | 526/281 |
| 4,570,011 | 2/1986 | So | 560/8 |
| 4,684,749 | 8/1987 | Paparatto | 568/797 |
| 4,783,514 | 11/1988 | Kirchhoff et al. | 526/281 |
| 4,822,930 | 4/1989 | Liu | 570/124 |
| 4,853,487 | 8/1989 | Nonn | 568/730 |
| 4,891,452 | 1/1990 | Nonn et al. | 568/730 |
| 4,999,449 | 3/1991 | Kirchhoff | 568/8 |

OTHER PUBLICATIONS

*Chem. Ber.*, vol. 93 (1960), pp. 1774-1781, L. Horner et al. Zur elektgrophilen substitution des benzocyclobutens.
*J. Org. Chem.*, vol. 40 (1975), pp. 3649-3650, T. Cohen et al., Copper(I)-Induced Reductive Dehalogenation, Hydrolysis, or Coupling of Some Aryl & Vinyl Halides at Room Temperature.
*Tetrahedron*, vol. 40 (1984), pp. 1433-1456, J. Lindley; Copper Assisted Nucleophilic Substitution of Aryl Halogen.
*Tetrahedron*, vol. 45 (1989) pp. 5565-5576, Henk L. Aalten et al.; The Copper Catalysed Reaction of Sodium Methoxidde with Aryl Bromides.
*J. Chem. Soc.* (C), (1969), pp. 312-315, R. G. R. Bacon et al.,; Metal Ions and Complexes in Organic Reactions.
*Russ Chem Rev.*, vol. 43 pp. 679-689, A. A. Moroz et al; Ullmann Ether Condensation.
*J. Org. Chem.*, vol. 29 (1964), pp. 3624-3626, H. Weingarten Mech. of Ullman Condensation.
*J. Org. Chem.*, vol. 29 (1964), pp. 977-978, H. Weingarten Ullman Condensation.
*J. Org., Chem.* vol. 32 (1967), pp. 2501-2505, A. L. Williams et al.; Solvent-assisted Ullmann, Ether Synthesis. Reactions of Dihydric Phenols.
*Australian J. of Chem.*, (1975), after p. 1741, W. D. Crow et al.
*Tetrahedron Letters*, vol. 22 (1977) pp. 1867-1870 J. M. Riemann et al.

*Primary Examiner*—Werren B. Lone
*Attorney, Agent, or Firm*—Charlotte M. Kraebel; Charles J. Enright

[57] ABSTRACT

A process for preparing a 3- or 4-hydroxybenzocyclobutene comprises reacting a 3- or 4-halogenzocyclobutene reactant with an alkali metal hydroxide by heating in an aqueous alcohol medium at a temperature from about 50° C. to a temperature at which dimerization or oligomerization of a benzocyclobutene reactant or product is a significant side reaction, in the presence of a metal-containing catalyst, for a time sufficient to convert the halobenzocyclobutene reactant to the hydroxybenzocyclobutene product.

28 Claims, No Drawings

PROCESS FOR PREPARING HYDROXYBENZOCYCLOBUTENES

CROSS-REFERENCE TO RELATED APPLICATION

This is a continuation of application Ser. No. 07/763,014, filed Sep. 20, 1991, now abandoned.

TECHNICAL FIELD

This invention relates to low temperature processes for preparing hydroxybenzocyclobutenes, which are useful as intermediates for specialty polymers. A low temperature process for preparing these intermediates is highly important, because benzocyclobutenes tend to polymerize through ring opening to orthoxylylene moieties at high temperatures. Accordingly, it is very desirable to provide a method for avoiding premature oligomerization or polymerization of benzocyclobutene compounds at high reaction temperatures, heretofore required for the preparation of phenols from aryl halides.

BACKGROUND ART

4-Hydroxybenzocyclobutene, has been prepared by diazotization and heating of the corresponding amine, Horner et al., Chem. Ber., vol. 93 (1960), pages 1774–1781. The yield of 4-hydroxybenzocyclobutene is about 50%.

So, in the U.S. Pat. No. 4,570,011, has proposed the synthesis of hydroxybenzocyclobutenes by pyrolysis of a chloromethyl methylbenzoate precursor.

Paparatto, in U.S. Pat. No. 4,684,749, has proposed, converting iodobenzene to phenol in the presence of a basic acidity acceptor in the liquid phase, in the presence of a copper-containing catalyst. The acidity acceptor can be NaOH or KOH. A methanol/water solvent system gave 64% conversion of iodobenzene, with a selectivity to phenol of 50% and a selectivity to anisole of 47%. Use of an aqueous toluene solvent system gave significantly higher selectivity toward phenol.

Hale, in U.S. Pat. No. 2,028,055, has proposed simultaneous hydrolysis and ammonolysis of aryl halides at temperatures from 150° C. to 260° C., preferably at 200°–240° C. The catalyst comprises a cuprous, silver, cobaltic or zinc compound.

Hale, in U.S. Pat. No. 1,882,824, has also proposed converting chlorobenzene to phenol by reaction with sodium carbonate in the presence of copper metal at 250°–375° C.

Smith et al., in U.S. Pat. No. 4,001,340, have recited hydrolyzing haloaromatic compounds by concentrated aqueous hydroxide solutions at 250°–330° C. A copper catalyst is used.

Poffenberger, in U.S. Pat. No. 2,137,587, teaches preparation of phenol by hydrolysis of chlorobenzene with excess sodium hydroxide solution at 350°–400° C. under pressure.

It is the object of this invention to provide highly selective, high yield, low temperature processes for the preparation of hydroxybenzocyclobutene compounds so as to prevent premature oligomerization or polymerization of resulting hydroxy-benzocycobutene products.

DISCLOSURE OF THE INVENTION

This invention relates to a process for preparing 3- or 4-hydroxybenzocyclobutene, comprising reacting a 3- or 4-halobenzocyclobutene reactant with an alkali metal hydroxide in an aqueous alcohol medium by heating at a temperature from about 80° C. to a temperature at which dimerization or oligomerization of a benzocyclobutene reactant or product is a significant side reaction, in the presence of a metal-containing catalyst, for a time sufficient to convert the halobenzocyclobutene reactant to the hydroxybenzocyclobutene product.

DETAILED DESCRIPTION OF THE INVENTION

"Benzocyclobutene," as used in the specification and claims, includes carbocyclic and heterocyclic arylcyclobutene (cyclobutarene) compounds, which consist of a cyclobutene ring fused to an aromatic carbocyclic or heterocyclic ring. Aromatic as used herein refers to carbocyclic or heterocyclic rings in which $4n+2$ delocalized pi electrons are contained in an orbital ring. This property is also known as resonance stabilization or delocalization.

Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenyl cycloalkane radicals. The most preferred carbocyclic aromatic radical is a benzene radical, which, when fused to a cyclobutene ring, produces the simplest member of the series, benzocyclobutene.

Examples of preferred heterocyclic aromatic compounds include pyrrole, furan, thiophene, imidazole, oxazole, thiazole, pyrazine, pyridine and pyrimidine. More preferred heterocyclic aromatic radicals are pyridine, furan and thiophene, with cyclobutapyridine being most preferred. The carbocyclic analogs are preferred over the heterocyclic analogs.

Either the aryl radicals or the cyclobutene ring can be substituted by electron-donating or electron-withdrawing groups. Examples of such substituents include cyano, halo, carboxy, hydrocarbyloxy, carbonyl, alkanoyl, aroyl, alkylsulfonyl, alkylsulfonoyl, amido, alkyl, alkenyl or aryl groups.

It will be understood that "benzocyclobutene" is an art-recognized term. In the commonly-used non-systematic numbering system for benzocyclobutenes, the 1-and 2-positions are in the cyclobutene ring. The 3-and 6-positions are in an aromatic ring, adjacent to the cyclobutene ring. The 4- and 5-positions are meta- to the cyclobutene ring. The simplest member of the series, benzocyclobutene, is formally identified as bicyclo[4.2.-0]octa-1,3,5-triene. A compound, formally identified as 3-bromobicyclo[4.2.0]octa-1,3,5-triene, is commonly known as 4-bromobenzocyclobutene. The common names will be used in the specification and claims.

The hydroxybenzocyclobutene products of this invention can be used for the preparation of bridged benzocyclobutenes of the formula

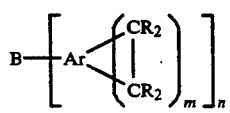

wherein B is an n-valent bridging moiety containing oxygen, bonded to the aromatic ring (Ar) of the benzocyclobutene unit, m is an integer of 1 or more, n is an integer of 2 or more and each R is hydrogen or an electron-donating or electron-withdrawing substituent.

In the simplest cases, the cyclobutene ring is unsubstituted (each R is H and m is 1) and the aromatic ring is benzene. This case can be represented by the subgeneric formula

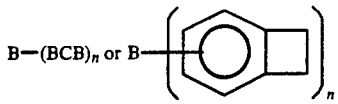

wherein B is the oxygen-containing bridging function and n is as above. In this formula, BCB represents 3- or 4-benzocyclobutenyl.

Examples of oxygen-containing bridging groups include, but are not limited to,

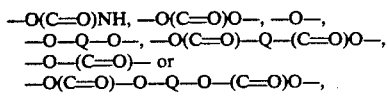

wherein Q is a divalent bridging group, such as phenylene, xylylene, tolylene, arylene-alkylene-arylene, alpha, omega-alkylene and the like.

A particularly preferred bridging group is the carbonate group. In the simplest case, the product is of the formula

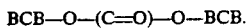

Other carbonates are those derived, for example, from diphenolic compounds, such as hydroquinone or bisphenol A. These are represented by the formulas

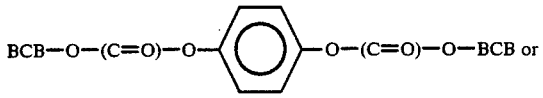

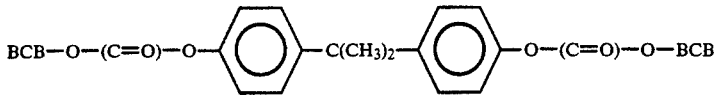

respectively.

The hydroxybenzocyclobutene may be used to end cap a polycarbonate such as in the formula

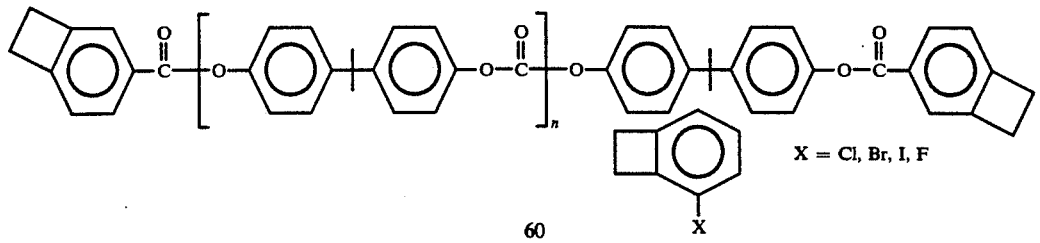

wherein n is a number greater than 1.

A procedure for this process is disclosed in U.S. Ser. No. 633,740 filed Dec. 24, 1990 incorporated herein by reference.

Other preferred bridging groups include ester groups, such as terephthaloyloxy or adipoyloxy, which produce bridged derivatives of the formula

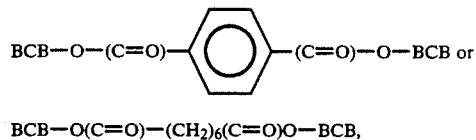

respectively.

Another preferred type of bridging group is that wherein Q is alkylene and the simplest products correspond to the general formula

in which x is an integer from 2-20. Most preferred bridging groups include those derived by reaction with an alkylene glycol, such as 1,4-butanediol or 1,6-hexanediol.

Corresponding oxaalkylene glycols can be used as bridging groups. For example, B can be —OC$_{x/2}$H$_x$-OC$_{x/2}$H$_x$O—, wherein x is as above. Other oxygen-containing bridging groups are disclosed by Kirchhoff et al., U.S. Pat. No. 4,540,763, herein incorporated by reference.

Exemplary unbridged benzocyclobutene compounds which can be converted to hydroxybenxocyclobutenes in accordance with this invention include, but are limited to, compounds of the structures:

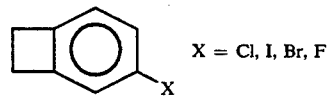

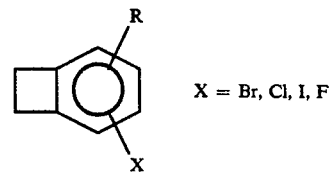

wherein R is alkyl, vinyl, substituted vinyl, ethynyl, substituted ethynyl, aryl, polyaryl, substituted aryl, substituted polyaryl, heterocyclic, heteroaryl, alkylaryl, alkylheterocyclic, arylheteroaryl, trialkylsilyl, nitro, cyanato, formyl, aroyl, alkanoyl, benzobicyclobutenyl, benzocyclobutenoyl, alkylbenzocyclobutenyl, arylbenzocyclobutenyl, alkylarylbenzocyclobutenyl, arylalkylbenzocyclobutenyl, oxybenzocyclobutenyl, thiobenzocyclobutenyl, benzocyclobutenyl sulfonyl, benzocyclobutenyl sulfoxide, carboxy, carbalkoxy, mono or dialkylamino, mono or diarylamino, mono or diheterocyclic amino, mono or diheteroaryl amino, hydroxy, alkoxy aryloxy, substituted alkoxy, substituted aryloxy, polyaryloxy, substituted polyaryloxy, mercapto, alkylthio, substituted alkylthio, arylthio, substituted arylthio, polyarylthio, substituted polyarylthio, heterocyclothio and heteroarylthio. Substituted compounds include hydrocarbyl substituents, as recited by Kirchhoff, supra.

Representative higher fused ring benzocyclobutene reactants include, but are not limited to, compounds of the formulas:

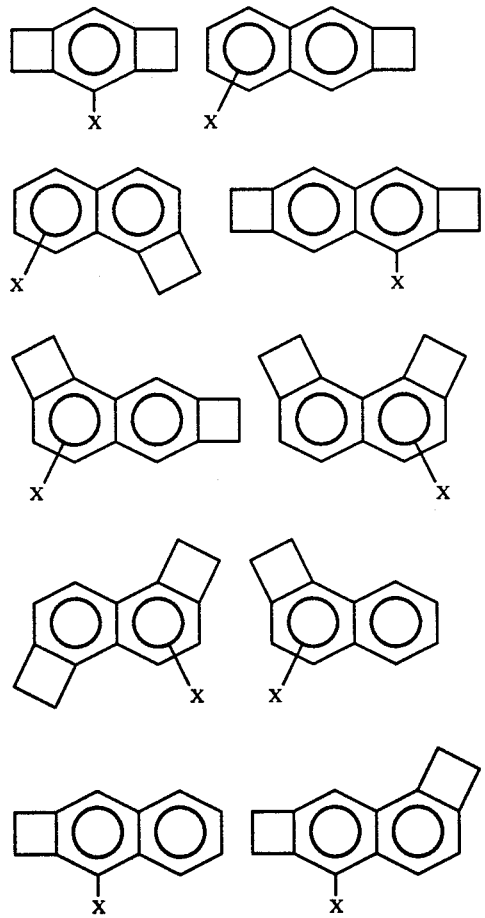

wherein X is Cl, Br or I.

It will be understood that the fused ring benzocyclobutenes can be substituted as above and that dihalo compounds can also be used.

Preferred reactants for the practice of this invention are those containing a 3- or 4-halobenzocyclobutene moiety, more preferably a 4-halobenzocyclobutene moiety. Preferred halobenzocyclobutenes include the bromo, chloro and iodo compounds. The most preferred benzocyclobutene reactant is 4-bromobenzocyclobutene.

Monobrominated cyclobutarenes, particularly 4-bromobenzocyclobutene, can be prepared as recited by Liu, U.S. Pat. No. 4,822,930, herein incorporated by reference.

The metal-containing catalyst can be selected from heavy metals or their compounds, including but not limited to, elemental iron or copper, as well as compounds of copper (I), copper (II), iron (II), iron (III), cobalt (II), nickel (II) or nickel (I).

Preferred metal-containing catalysts are elemental copper or copper compounds. Representative copper (I) compounds include, but are not limited to, the cyanide, iodide, sulfate, acetate, benzoate, bromide, chloride, isopropenylacetylide, nitride, phenylacetylide, thiocyanate or triflate. Copper (II) compounds include, for example, the sulfate, acetate, borate, bromate, bromide, carbonate, chloride, cyanide, formate, nitrate, oxalate and salicylate.

Copper includes copper metal, whether in the form of dust, wire or mesh, as well as copper bronze. Copper (I) and copper (II) compounds also include products, obtained by disproportionation of copper metal or another reducing agent, with copper (II) compounds. This reaction can be represented by the equation:

$$CuX_2 + Cu^\circ \rightleftharpoons 2\ CuX$$

wherein X=Cl, Br, I or ½ O.

Particularly, preferred copper-containing catalysts include cuprous oxide, cuprous bromide, cupric sulfate and cupric acetate. Most preferred are cuprous bromide and cuprous oxide.

The molar ratio of benzocyclobutene reactant to metal-containing catalyst is from about 500:1 to about 1:1. Preferably, the ratio is from about 100:1 to 1:1, most preferably from about 50:1 to about 1:1.

Alkali metal hydroxides include lithium hydroxide, sodium hydroxide, potassium hydroxide, cesium hydroxide and rubidium hydroxide. It is preferred to use sodium or potassium hydroxide, most preferably sodium hydroxide.

The molar ratio of benzocyclobutene reactant to alkali metal hydroxide is from about 1:2 to about 1:1000. The preferred range is from about 1:2 to about 1:50, most preferably from about 1:2 to about 1:5.

The temperature for performing the process of this invention is from about 50° C. to a temperature at which dimerization or oligomerization of the benzocyclobutene reactant or product becomes a significant side reaction. The upper temperature limit can be determined empirically, by known methods, such as following the progress of the reaction using gas chromatography. It has been found that appreciable dimerization or oligomerization occurs at temperatures above 200° C., or even above 180° C. Therefore, it is preferred to carry out the process of this invention from about 100° C. to about 180° C. More preferably, the reaction is carried out from 140° C. to about 170° C., most preferably, from about 140° C. to about 165° C.

The time required for conversion of halobenzocyclobutene to hydroxybenzocyclobutene is a function primarily of the reaction temperature and can be determined empirically, as above. At a representative temperature of 160° C., substantially complete conversion of bromobenzocyclobutene to hydroxybenzocyclobutene occurs with seven hours heating.

The aqueous alcohol medium can contain a primary or secondary alcohol, although it is preferred to use a primary alcohol. Methanol, ethanol, isopropanol, butanol, 2,2,2-trifluoroethanol, benzyl alcohol and polyethylene glycol are representative. Particularly advantageous results are obtained using methanol, ethanol, 2,2,2-trifluoroethanol or benzyl alcohol, which are, therefore, preferred. The product of reactions, run with aqueous benzyl alcohol, contains benzyloxybenzocyclobutene as a by-product. This mixture can be readily converted to hydroxybenzocyclobutene by hydrogenolysis.

The ratio of alcohol to water in the aqueous alcohol medium can be varied from about 10:1 to about 1:10 by volume. Preferably ratios of alcohol to water are from about 3:1 to about 0.5:1, most preferably about 2:1 to about 0.5:1.

The ratio of aqueous alcohol medium to halobenzocyclobutene can be varied from about 100:1 to about 1:1 by weight. It is preferred to use ratios of 15:1 to 1:1, most preferably from about 10:1 to about 1:1.

A preferred process is that wherein the halobenzocyclobutene reactant is 4-bromobenzocyclobutene, the alcohol is methanol or ethanol, the catalyst is a copper compound and the temperature is from about 140° C. to about 165° C.

A preferred procedure for working up the reaction mixtures thus obtained comprises the steps of extracting a resulting reaction mixture with an aromatic hydrocarbon solvent and acidifying a resulting extracted water layer containing 3- or 4-MO-benzocyclobutene compound, wherein M is an alkali metal cation, at a temperature below ambient to convert the resulting MO-benzocyclobutene compound to a corresponding hydroxybenzocyclobutene. The alkali metal cation is selected from lithium, sodium, potassium, rubidium or cesium. For reasons of economy, the use of sodium hydroxide (M is Na+) is preferred.

Aromatic hydrocarbon solvents can be selected from benzene, toluene, xylenes, mesitylene or mixtures thereof. Toluene is preferred.

It is preferred to carry out the neutralization under conditions such that the acid, used for neutralization, does not attack the benzocyclobutene ring to produce side products. Accordingly, the temperature for neutralization is usually from about 0° C. to about 30° C. More preferably, neutralization is carried out at 2°–15° C.

Reaction mixtures thus treated are preferably those obtained wherein:

(a) conversion of the halobenzocyclobutene reactant is carried out at a temperature below about 165° C., (b) aqueous alcohol medium is used at a weight ratio to halobenzocyclobutene reactant equal to or below about 15; and (c) alkali metal hydroxide and halobenzocyclobutene reactant are used at molar ratios of about 2-5:1.

The resulting mixture is preferably further purified by isolating a resulting hydroxybenzocyclobutene product by extraction into an aromatic solvent, drying the resulting solution, stripping aromatic solvent from the resulting solution and distilling the resulting residue by short path distillation. Products isolated in this fashion routinely exceed 98% purity. An optional preliminary step comprises removing volatile solvents, including excess alcohol, by distillation using a rotary evaporator.

The process of converting halobenzocyclobutenes to hydroxybenzocyclobutenes in a direct one-step process, catalyzed by metal-containing compound, is particularly advantageous because the low reaction temperature results in a very low degree of oligomerization or polymerization. The products of the one-step reaction can be purified, by a combination of extraction and distillation, to a purity above 98%.

It has also been found that the volume of reactants in closed reactor significantly affects the outcome of the reaction. It is preferred that at least 50% of the reactor volume be occupied by the reactants. Most preferably, the reactor volume is at least ⅔ full with liquid reactants.

The process of this invention can be carried out in any container, with or without a stirring attachment, which can be heated to the required temperature, which can withstand pressures of 3-75 atm and which is not attacked by the reactants, catalysts or products of the invention.

Cyclobutapyridines can be prepared by the pyrolysis of 4-pyridyl propargyl ether at 550° C. See J. M. Riemann et al., *Tetrahedron Letters*, no. 22 (1977), pages 1867–1870. Alternatively, a pyridine-4-carbonitrile, having an alkyl substituent on the carbon atom adjacent to the nitrile, is reacted with sodium azide and ammonium chloride in N,N-dimethylformamide to prepare a 5-(alkyl-4-pyridyl)tetrazole. The 5-(alkyl-4-pyridyl)tetrazole is pyrolyzed at about 600° C. to a cyclobutapyridine. See W. D. Crow et al., *Australian Journal of Chemistry* (1975), after page 1741. 2-Bromocyclobuta[b]pyridine can be prepared from 2-hydroxy[b]cyclobutapyridine. See Kirchhoff et al., U.S. Pat. No. 4,783,514, herein incorporated by reference.

BEST MODE FOR CARRYING OUT THE INVENTION

Most preferably, the process of this invention is that wherein the halobenzocyclobutene reactant is 4-bromobenzocyclobutene, the alcohol is methanol or ethanol, the catalyst is a copper compound and the temperature is from about 140° C. to about 165° C.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperature are set forth uncorrected in degrees Celsius. Unless otherwise indicated, all parts and percentages are by weight.

EXAMPLE 1

Conversion of 4-Bromobenzocyclobutene to 4-Hydroxybenzocyclobutene; Cuprous Bromide Catalyst (a) To a 300-mL Parr bomb reactor, equipped with a mechanical stirrer and heating jacket, are charged 9.1 g of 4-bromobenzocyclobutene, a solution of 10 g of NaOH in 60 mL of water, 90 mL or methanol and 1 g of cuprous bromide. The reactor is flushed with nitrogen and sealed. The sealed reactor is heated at 160° C. for 7 hours.

The reaction mixture is cooled to room temperature and the bomb is opened. Volatile materials are removed on a rotary evaporator. The residue is diluted with 100 mL of water. The aqueous solution is extracted with two 50-mL portions of methylene chloride. The methylene chloride extract contains small amounts of unreacted 4-bromobenzocyclobutene (about 5%) and neutral materials, including 4-methoxybenzocyclobutene (about 5%), by GC analysis.

The aqueous solution is cooled to 0° C., acidified with dilute HCl (20%) and extracted with three 50-mL portions of methylene chloride. The organic layer is washed with saturated sodium chloride solution, dried over anhydrous magnesium sulfate and passed through a bed of silica gel. Removal of solvent gives 4.2 g of 4-hydroxybenzocyclobutene (70%). M.p., 47° C.

(b) An experiment, otherwise as in (a), using potassium hydroxide instead of sodium hydroxide, gives a similar yield of 4-hydroxybenzocyclobutene.

(c) An experiment, similar to (a), is done by heating at 140° C. After 18 hours, at 140° C., the reaction mixture contains significant amounts (32%) of unreacted 4-Br-BCB.

EXAMPLE 2

Effect of Copper Catalysts on Conversion of 4-Bromobenzocyclobutene to 4-Hydroxybenzocyclobutene Experiments are run, as in Example 1, heating similar reaction mixtures at 160° C. for 7 hours using various copper-containing catalysts. The following results are observed:

| Catalyst | 4-HO-BCB (% isolated) |
| --- | --- |
| $Cu_2Br_2$ | 72 |
| $CuSO_4.5H_2O$ | 65 |
| $Cu(OAc)_2$ | 66 |
| $Cu_2Br_2$ + pyridine | 59 |

These results show that a variety of copper compounds can catalyze the displacement of a bromine atom in 4-bromobenzocyclobutene by hydroxyl.

EXAMPLE 3

Reaction between 4-Bromobenzocyclobutene and Sodium Hydroxide in Aqueous Solution An aqueous solution containing 5 equivalents of sodium hydroxide to 4-Br-BCB and cuprous bromide catalyst (7-10 mol %) is heated in a Parr bomb reactor with vigorous stirring for 6 hours at 180° C. The yield of 4-hydroxybenzocyclobutene is 30-45%. 4-Hydroxybenzocyclobutene is not formed in significant amounts at reaction temperatures below 180° C.

This experiment shows that an alcohol cosolvent improves conversion of 4-bromobenzocyclobutene to 4-hydroxybenzocyclobutene.

EXAMPLE 4

Effect of Cosolvent on Conversion of 4-Bromobenzocyclobutene to 4-Hydroxybenzocyclobutene Experiments are run as in Example 1, using various cosolvents, other than methanol. The following results are obtained:

| Solvent | Results |
| --- | --- |
| 1,2-dimethoxyethane | trace of 4-HO-BCB; mostly unreacted 4-Br-BCB |
| isopropanol | 10% 4-HO-BCB; mostly unreacted |
| tetrahydrofuran | Br-BCB trace of 4-HO-BCB, mostly unreacted Br-BCB |

EXAMPLE 5

Effect of Alcohol Concentration on Product Distribution

Experiments are run as in Example 1, in which the amount of methanol in the reaction mixture is varied. The following results are obtained:

| % Methanol (by vol) | 4-OH-BCB (isolated) |
| --- | --- |
| 40 | 69 |
| 50 | 71 |
| 60 | 72 |
| 90 | 43 |

These results show that optimum results are obtained when methanol constitutes 40-60% (by volume) of the solvent mixture.

EXAMPLE 6

Effect of Reactant Concentration on Product Distribution

Experiments are run as in Example 1, varying the volume of solution in the reactor and the concentrations of reactants. The following results are obtained:

| Br-BCB (mole) | Volume (mL) (water plus methanol) | % 4-HO-BCB (isolated) |
| --- | --- | --- |
| 0.05 | 150 | 70 |
| 0.1 | 300 | 72 |
| 0.2 | 300 | 72 |
| 0.25 | 300 | 55-62 |
| 0.3 | 300 | 55-61 |

At higher levels of 4-Br-BCB in the feed, the conversion to 4-methoxybenzocyclobutene increases and the yield of 4-hydroxybenzocyclobutene falls.

EXAMPLE 7

Large Lab Scale Evaluation of Process Parameters

Two-liter reactions are carried out in a Parr (series 4642) 2-L reactor, located in a high pressure cubicle, and equipped with two six-blade impellers on the stirrer shaft, a 136 atm (gauge) rupture disc, an air-driven stirrer motor and a liquid phase double-valved sampling tube. The reactor has a gas inlet valve, connected to a pressure gauge and a nitrogen cylinder. The reactor has a vent valve, connected to an exhaust line, which terminates at the roof of the building. A heating mantle, controlled from outside the cubicle, is used as heat source.

Ten-liter reactions are run in a 10-L jacketed glass reactor with a five-headed top, supported by a steel structure in a large walk-in hood with a bottom catch tray. The baffled reactor has a flush-mounted, double-valved bottom dump, and is fitted with a 2-L addition funnel, a nitrogen purge line, a thermocouple port and an air-driven polytetrafluoroethylene shafted stirrer. The nitrogen purge on the reactor is vented through a condenser and then a bubble design caustic scrubber trap to neutralize any acidic vapors. The jacket temperature is maintained using a Forma Scientific floor model (#2325) temperature-controlled bath and circulation system.

short path evaporations are done using a Leybold-Heraeus short-path distillation system (model KDL-4), equipped with a Triavac "A" dual stage rotary vane pump (model D2A, filled with Leybold HE-175 vacuum pump oil), an oil diffusion pump and a vacuum indicator (Thermovac TM 210). The oil jacket temperature is controlled with 1° C. using a Neslab model EX-250 HT high temperature circulating bath with temperature controller and digital readout. The internal condenser temperature was controlled by a flow of cooling water. The distillation unit has a high-efficiency, self-cleaning, roller-wiper system to form a thin film with short residence time under low pressures, achieved using an oil diffusion pump.

Reaction products are analyzed using a Hewlett-Packard 5710A gas chromatograph with FID detector, HP 3390A integrator, autosampler using a J&W 30-meter narrow bore column (1.0 micrometer capillary column), bonded with DB-1. The column pressure is 1.088 atm (gauge), the column flow 8 cc/min, column flow and makeup 25 cc/min, hydrogen pressure 37 cc/min, air pressure 360 cc/min and split flow 90 mL/min. The oven temperature is held at 100° C. for 2 min. and then program ramped at 8° C./min to 250° C. The injector temperature is 250° C. and the detector is at 300° C. Samples are loaded by a needle flash technique.

Size exclusion chromatography is run on equipment manufactured by TSK (Tosoh Corp.) using a G1000-HXL column of 7.8 mm i.d. and 30 cm length with a guard column HXL-L of 6 mm i.d. and 4 cm length. The absorbance detector is from Applied Biosystems, model 757, variable wavelength. Spectra are taken at 290 mn using a Waters 501 HPLC pump set at 1 mL/min with a Spectra-Physics SP4270 integrator. The sample concentration is 500 ppm in tetrahydrofuran. The retention times for dimer and trimer peaks appear at 8.6 min. and 7.7 min., respectively. The monomer peak appears at 10.3 min.

To the Parr reactor is charged 4-bromobenzocyclobutene, copper-containing catalyst, aqueous sodium hydroxide solution, solvent and water. The reactor is sealed and placed in a heating block assembly in the high pressure cubicle. The stirrer is attached and turned on. The system is purged three times with nitrogen (about 10.2 atm gauge). The nitrogen pressure is maintained for several minutes to check the reactor for leaks. The reactor is heated to the reaction temperature and held for desired time.

At the end of the reaction, the reactor is cooled and vented and the stirrer is turned off. The reactor is transferred to a hooded area and opened. The contents are poured into a plastic jug, using 250 mL of water to rinse out the reactor. The washings are combined with the reaction mixture. A samples of the resulting material is submitted for analysis. Optionally, the mixture at this point can be reduced in volume by evaporation of volatile materials, including excess alcohol, by distillation using a rotating evaporator.

A batch of reaction mixture is transferred to a 5-L flask, equipped with a bottom dump valve, and diluted with 250 mL of toluene. The resulting two-phase mixture is stirred vigorously for 10 min. and the phases are allowed to separate. The water layer is removed through the bottom dump. GC analysis of the top organic layer demonstrates that the contents are mainly unreacted 4-bromobenzocyclobutene and, in the case of alcohol solvent, 4-alkoxybenzocyclobutene. The aqueous layer contains primarily 4-hydroxybenzocyclobutene sodium salt, along with small amounts of unreacted 4-Br-BCB and 4-alkoxy-BCB.

The water layer is washed with two additional 250-mL portions of toluene as above. The resulting water layer is transferred to a 5-L round bottom flask, equipped with an overhead mechanical stirrer. The flask is placed in an ice bath and cooled to 5° C. The cooled contents of the flask are stirred while being acidified with concentrated HCl, added dropwise. The rate of addition is such that the temperature of the mixture does not exceed 15° C. At the end of the acidification, the mixture is poured into a 5-L round-bottom flask, equipped with a bottom dump valve, flask and diluted with 350 mL of toluene. The resulting mixture is stirred vigorously for 5 min and allowed to separate. The bottom layer is removed through the bottom dump. The top layer is saved. The bottom aqueous layer is washed with another 350 mL portion of toluene, as above. The combined toluene layers are washed with two 300-mL portions of saturated sodium chloride solution and dried over anhydrous sodium sulfate (about 40 g). Solvent is stripped from the dried solution using a rotary evaporator. The resulting oily residue contains 4-hdyroxybenzocyclobutene and a small amount of 3,3'-dihydroxybenzocyclooctadiene (GC).

Batches of product from the 10-L reactor are processed in a similar fashion.

Final purification of the product comprises two distillations in a short-path evaporator. Circulating baths for the column wall and condenser were set to the selected temperatures and allowed to heat up. After closing the nitrogen bleed valve, the vacuum pump trap and two receiving flasks were connected to the apparatus. The vacuum pump trap is immersed in a Dry Ice/acetone bath and the cold finger in the trap is filled with a Dry Ice/acetone mixture. After closing the stopper in the addition funnel, the vacuum gauge and vacuum pump are turned on. The system is evacuated to 2 torr and heated at 50° C. during addition of material at a rate of 5 mL/min. Toluene (about 15% of undistilled oil) is collected in the Dry Ice/acetone trap and heavies in the receiving flask.

During a second distillation, the evaporator column is heated to 95° C., the cold finger is set at 50° C. and the vacuum is maintained at 1 torr. The contents of the heavies in the receiving flask are fed to the still at a rate of 8-10 mL/min. The collected 4-hydroxybenzocyclobutene is a colorless oil, which crystallizes (needles) upon standing or sparging with nitrogen.

(a) Effect of Solvent

Experiments are done, using various cosolvents or cocatalysts:

| Solvent | Cosolvent/Cocatalyst | Result |
|---|---|---|
| THF | — | no reaction |
| tert-BuOH | EtOH | no reaction |
| THF | Bu$_4$N$^+$X$^-$ | no reaction |
| THF | HO(CH$_2$CH$_2$O)$_8$H | 25% BCB-OH BCB-O(CH$_2$CH$_2$O)$_8$H |
| HOCH$_2$CH$_2$OH | — | no reaction 61% BCB-OH |
| CF$_3$CH$_2$OH | — | BCB-OCH$_2$CF$_3$ |

These experiments show that at least some unbranched primary alcohol is required for the reaction.

(b) Effects of Concentration

The amount of Br-BCB is varied in reactions in aqueous ethanol, other factors remaining constant. The following results are obtained:

| Br-BCB (g) | mL EtOH + water g BCB-Br | BCB-OH (g) | Selectivity % OH/% OEt | mg BCB-OH mL reactor volume |
|---|---|---|---|---|
| 91 | 16.5 | 26 | 6.0 | 9 |
| 110 | 8.3 | 4.9 | 5.8 | 25 |
| 222 | 4.1 | 106 | 3.4 | 53 |
| 349 | 2.6 | 152 | 2.3 | 76 |
| 530 | 1.7 | 216 | 2.6 | 108 |

These results show that BCB-OH yield increases as a function of increasing the BCB-Br used in the reaction, but that selectivity is decreased. Reactor volume efficiency (mg BCB-OH/mL reactor volume) also increases with increasing Br-BCB, charged to the reaction.

Similar experiments are run in methanol, with the following results being obtained:

| Br-BCB (g) | mL MeOH + water g BCB-Br | Selectivity % OH/% OMe |
|---|---|---|
| 68 | 15 | 6 |
| 204 | 5 | 2.3 |
| 400 | 2.6 | 3.8 |

(c) Effect of Temperature in Ethanol/Water System

The following results are obtained:

| Temp (°C.) | Time (h) | Pressure (atm) | % BCB-Br (converted) | % OH/% OEt | % Dimer (GC) |
|---|---|---|---|---|---|
| 140 | 27 | 5.10 | 90 | 2.4 | 2 |
| 150 | 9 | 6.80 | 80 | 2.3 | 1 |
| 160 | 9 | 8.84 | 97 | 2.3 | 4.2 |

These experiments show that increasing the reaction temperature from 140° C. to 160° C. results in increased conversion, without significant loss of selectivity. Some increase in dimerization occurs at 160° C.

(d) Effect of Temperature in Methanol/Water System

| Temp (°C.) | Time (h) | Pressure (atm) | % BCB-Br (converted) | % OH/% OMe | % Dimer (GC) | % Polymer (LC) |
|---|---|---|---|---|---|---|
| 140 | 23.5 | 6.46 | 71 | 2.3 | 0.5 | 3 |
| 150 | 13.8 | 8.16 | 98 | 3.2 | 1.4 | 7 |
| 160 | 9.2 | 10.2 | 98 | 2.2 | 4.6 | 11 |
| 180 | 5.0 | 25.17 | 99 | 2.9 | 9.5 | tar |

These results show that increasing the reaction temperature increases conversion of BCB-Br, but also increases dimerization and oligomerization.

(e) Effect of Variation in Caustic/Br-BCB Ratios, Ethanol/Water System

| NaOH/Br-BCB (moles) | % BCB-Br (converted) | % OH/% OEt |
|---|---|---|
| 5 | 97 | 2.3 |
| 3.3 | 95 | 2.5 |
| 2.4 | 67 | 4.2 |

(f) Effect of Ethanol/Water Ratio

| BCB-Br (g) | EtOH (mL) | Water (mL) | EtOH/Water | BCB/OH (g) | BCB-OH (% yield) |
|---|---|---|---|---|---|
| 183 | 800 | 400 | 2.0 | 60 | 51 |
| 349 | 540 | 367 | 1.5 | 152 | 60 |
| 352 | 300 | 603 | 0.5 | 37 | 14 |

These experiments show that increasing the ethanol/water ratio improves the yield of BCB-OH.

(g) Effect of Catalyst Concentration

| BCB/Br (g) | BCB-Br/CuBr (moles) | BCB-OH (g) | BCB-OH (% yield) | % OH/% OEt |
|---|---|---|---|---|
| 349 | 7 | 152 | 60 | 2.3 |
| 348 | 14 | 147 | 58 | 2.3 |
| 358 | 29 | 150 | 58 | 2.3 |

These experiments show that the reaction is relatively insensitive to catalyst concentrations.

EXAMPLE 8

Reaction Between 4-Bromobenzocyclobutene and Benzyl Alcohol

A reaction is run as in Example 7, using as cosolvent benzyl alcohol. The product, worked up as in Example 7, contains 4-hydroxybenzocyclobutene and 4-benzyloxybenzocyclobutene. The latter can be hydrogenolyzed to 4-hydroxybenzocyclobutene and toluene by treatment with hydrogen.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for preparing a 3- or 4-hydrooxybenzocyclobutene compound, comprising reacting a 3- or 4-halobenzocyclobutene compound, selected from fluoro-, chloro-, bromo-, or iodobenzocyclobutene compounds, with an alkali metal hydroxide in the presence of a catalytic amount of elemental copper or a copper compound in an aqueous alcohol medium at a temperature from about 50° C. to a temperature at which dimerization or oligomerization of a benzocyclobutene reactant or product is a significant side reaction, for a time sufficient to convert the halobenzocyclobutene reactant to the hydroxybenzocyclobutene product.

2. The process of claim 1, wherein the temperature is from about 140° C. to about 170° C.

3. The process of claim 1, wherein the temperature is from about 140° C. to about 165° C.

4. The process of claim 1, wherein the catalyst is cuprous bromide.

5. The process of claim 1, wherein the catalyst is cupric sulfate.

6. The process of claim 1, wherein the catalyst is cupric acetate.

7. The process of claim 1, wherein the alcohol is a primary alcohol.

8. The process of claim 1, wherein the alcohol is methanol.

9. The process of claim 1, wherein the alcohol is ethanol.

10. The process of claim 1, wherein the alcohol is 2,2,2-trifluoroethanol.

11. The process of claim 1, wherein the alcohol is benzyl alcohol.

12. The process of claim 1, wherein the halobenzocyclobutene reactant is 4-bromobenzocyclobutene.

13. The process of claim 1, wherein the halobenzocyclobutene reactant is 4-bromobenzocyclobutene, the alcohol is methanol or ethanol, the catalyst is a copper compound and the temperature is from about 140° C. to about 165° C.

14. The process of claim 1, wherein the alcohol is benzyl alcohol and a resulting mixture of hydroxyphenzocyclobutene and benzyloxybenzocyclobutene is subjected to hydrogenolysis.

15. In a process for converting a 3- or 4-halobenzocyclobutene compound, selected from fluoro-, chloro-, bromo-, or iodobenzocyclobutene compounds, to a corresponding 3- or 4-hydroxybenzocyclobutene product in an aqueous alcohol medium in the presence of a catalytic amount of elemental copper or a copper compound and an alkali metal hydroxide at an elevated temperature from about 50° C. to a temperature at which dimerization or oligomerization of a benzocyclobutene reactant or product is a significant side reaction for a time sufficient to convert the halobenzocyclobutene reactant to the hydroxybenzocyclobutene product, the improvements comprising extracting a resulting reaction mixture with an aromatic hydrocarbon solvent and acidifying a resulting water layer containing 3- or 4-MO-benzocyclobutene compound to a corresponding hydroxybenzocyclobutene, wherein M is an alkali metal cation, at a temperature below ambient to convert the resulting MO-benzocyclobutene compound to a corresponding hydroxybenzocyclobutene.

16. The process of claim 15, wherein
   (a) conversion of the halobenzocyclobutene reactant is carried out at a temperature below about 165° C.,
   (b) aqueous alcohol medium is used at a weight ratio to halobenzocyclobutene reactant equal to or below about 15; and
   (c) alkali metal hydroxide and halobenzocyclobutene reactant are used at molar ratios of about 2-5:1.

17. The process of claim 15, wherein the alkali metal hydroxide is sodium hydroxide.

18. The process of claim 15, wherein the reaction mixture is extracted with toluene.

19. The process of claim 15, wherein neutralization is carried out under conditions such that an acid, used for neutralization, does not attack the benzocyclobutene ring to produce side products.

20. The process of claim 15, wherein neutralization is carried out at 2°-15° C.

21. The process of claim 15, wherein the halobenzocyclobutene reactant is 4-bromobenzocyclobutene.

22. The process of claim 15, wherein acidification is carried out with a mineral acid.

23. The process of claim 15, wherein the alcohol is ethanol.

24. The process of claim 15, wherein the alcohol is methanol.

25. The process of claim 15, wherein the catalyst is cuprous oxide.

26. The process of claim 15, including the further steps of isolating a resulting hydroxybenzocyclobutene product by extraction into an aromatic solvent, drying the resulting solution, stripping aromatic solvent from the thus-dried solution and distilling the resulting residue by short path distillation.

27. The process of claim 26, wherein the aromatic solvent is toluene.

28. The process of claim 1, wherein the copper compound is selected from the group consisting of copper (I) oxide, cyanide, iodide, sulfate, acetate, benzoate, bromide, chloride, isopropenylacetylide, nitride, phenylacetylide, thiocyanate and triflate; copper (II) oxide, sulfate, acetate, borate, bromate, bromide, carbonate, chloride, cyanide, formate, nitrate, oxalate and salicylate; or elemental copper or a mixture thereof.

* * * * *